United States Patent
Vickers et al.

(10) Patent No.: US 11,324,597 B2
(45) Date of Patent: *May 10, 2022

(54) IMPLANTABLE COMPOSITE CONTAINING CARBONATED HYDROXYAPATITE

(71) Applicant: Warsaw Orthopedic, Inc., Warsaw, IN (US)

(72) Inventors: Scott M. Vickers, Hernando, MS (US); Jeffrey L. Scifert, Arlington, TN (US); Ian R. Dunkley, Kingston (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/586,358

(22) Filed: Sep. 27, 2019

(65) Prior Publication Data

US 2020/0038187 A1   Feb. 6, 2020

Related U.S. Application Data

(63) Continuation of application No. 15/491,564, filed on Apr. 19, 2017, now Pat. No. 10,426,621.

(60) Provisional application No. 62/324,444, filed on Apr. 19, 2016.

(51) Int. Cl.
| | | |
|---|---|---|
| *A61F 2/28* | (2006.01) | |
| *A61L 27/36* | (2006.01) | |
| *A61L 27/46* | (2006.01) | |
| *A61L 27/58* | (2006.01) | |
| *A61K 6/17* | (2020.01) | |
| *A61K 6/802* | (2020.01) | |
| *A61K 6/838* | (2020.01) | |
| *A61F 2/30* | (2006.01) | |

(52) U.S. Cl.
CPC .................. *A61F 2/28* (2013.01); *A61K 6/17* (2020.01); *A61K 6/802* (2020.01); *A61K 6/838* (2020.01); *A61L 27/3608* (2013.01); *A61L 27/46* (2013.01); *A61L 27/58* (2013.01); *A61F 2002/2835* (2013.01); *A61F 2002/30032* (2013.01); *A61F 2002/30062* (2013.01); *A61F 2002/30677* (2013.01); *A61F 2310/00293* (2013.01); *A61F 2310/00359* (2013.01); *A61F 2310/00371* (2013.01); *A61L 2430/02* (2013.01)

(58) Field of Classification Search
CPC ........ A61L 27/3608; A61L 27/46; A61F 2/28; A61F 2002/2835
See application file for complete search history.

(56) References Cited

U.S. PATENT DOCUMENTS

| | | |
|---|---|---|
| 4,097,935 A | 7/1978 | Jarcho |
| 7,419,680 B2 | 9/2008 | LeGeros |
| 8,048,857 B2 | 11/2011 | McKay et al. |
| 8,163,030 B2 | 4/2012 | Maspero et al. |
| 8,652,503 B2 | 2/2014 | Wironen et al. |
| 8,673,017 B2 | 3/2014 | Martinetti et al. |
| 8,758,791 B2 | 6/2014 | McKay |
| 9,034,356 B2 | 5/2015 | Shimp et al. |
| 9,107,751 B2 * | 8/2015 | Winterbottom ......... A61L 27/56 |
| 2003/0055512 A1 | 3/2003 | Genin et al. |
| 2006/0233849 A1 | 10/2006 | Simon et al. |
| 2007/0191963 A1 | 8/2007 | Winterbottom et al. |
| 2012/0111226 A1* | 5/2012 | Bujoli ..................... C01B 25/45 |
| | | 106/35 |
| 2014/0067082 A1 | 3/2014 | Liu et al. |

FOREIGN PATENT DOCUMENTS

| | | |
|---|---|---|
| EP | 1958649 | 8/2008 |
| EP | 2228080 | 9/2010 |
| EP | 2228080 A1 | 9/2010 |

OTHER PUBLICATIONS

European Examination Report, European Patent Office, European Appl. No. 17 786 545.8, dated Oct. 26, 2020.
Iain R. Gibson et al: "Novel synthesis and characterization of an AB-type carbonate-substituted hydroxyapatite", Journal of Biomedical Materials Research, vol. 59, No. 4, Mar. 15, 2002 (Mar. 15, 2002), pp. 697-708.
Kannan S et al: "Synthesis, mechanical and biological characterization of ionic doped carbonated hydroxyapatite/-tricalcium phosphate mixtures", Acta Biomaterialia, Elsevier, Amsterdam, NL, vol. 7, No. 4, Dec. 6, 2010 (Dec. 6, 2010), pp. 1835-1843.
European Search Report for EP 17786545.8 dated Nov. 8, 2019 (7 pages).
Australian Patent Office, IP Australia, Examination report No. 1 for standard patent application; Application No. 2017254618; dated Oct. 6, 2020.
International Search Report and Written Opinion for PCT/US2017/28347, the counterpart application dated Jul. 24, 2017, 12 pages.
Owens, GJ et al., Sol-gel based materials for biomedical applications. Progress in Materials Science. vol. 77. Jan. 13, 2016. pp. 1-79; abstract; pp. 4, 14, 17, 32, 47-48.
Tadic, D et al., A thorough physicochemical characterisation of 14 calcium phosphate-based bone substitution materials in comparison to natural bone. Biomaterials. vol. 25. No. 6. 2004, pp. 987-994; abstract; figures1, 3b; pp. 987-990.

(Continued)

*Primary Examiner* — Brian A Dukert
(74) *Attorney, Agent, or Firm* — Sorell, Lenna & Schmidt LLP; William D. Schmidt, Esq.

(57) ABSTRACT

Provided is an implantable composite which includes a plurality of resorbable ceramic particles with or without a biodegradable polymer. The resorbable ceramic particles can be granules including carbonated hydroxyapatite and tricalcium phosphate in a ratio of 5:95 to 70:30. Some resorbable ceramic particles are granules, which include carbonated hydroxyapatite and β tricalcium phosphate in a ratio of 5:95 to 70:30. The resorbable ceramic particles have a particle size from about 0.4 to about 3.5 mm. The implantable composite is configured to fit at or near a bone defect as an autograft extender to promote bone growth. Methods of using the implantable composite are also provided.

17 Claims, No Drawings

(56) References Cited

OTHER PUBLICATIONS

Sadeghilar, A et al., Local Tissue Reaction and Biodegradation of Hydroxyapatite/Tricalcium Phosphate Composites. World Journal of Medical Sciences. vol. 11. No. 3. pp. 301-305. 2014; entire document.

L.T. Bang et al, "Carbonate Hydroxyapatite and Silicon-Substituted Carbonate Hydroxyapatite: Synthesis, Mechanical Properties, and Solubility Evaluations", The Scientific World Journal; vol. 2014, Abstract 8pp.

E Landi et al, "Influence of Synthesis and Sintering Parameters on the Characteristics of Carbonate Apatite", Institute of Science & Technology for Ceramics; 2003; pp. 1763-1770.

E. Landi et al., "Carbonated Hydroxyapatite as Bone Substitute", Journal of the European Ceramic Society; vol. 23, Issue 15, 2003; Abstract, 1p.

Gibson et al., "Novel Synthesis and Characterization of an AB-type Carbonate-substituted Hydroxyapatite", J. Biomed Mater Res, Mar. 2002; Abstract 1 p.

G. Spence et al., "Bone Formation in a Carbonate-substituted hydroxyapatite Implant is inhibited by Zoledronate", Orthopaedic Research Unit, Univ of Cambridge, England; vol. 90-B, No. 12, Dec. 2008; pp. 1635-1640.

Technical Guide, "Mastergraft Putty", Medtronic Sofamor Danek USA, Inc; 2006; 12pp.

Technical Guide, "Mastergraft Granules; Mini Granules; Putty", Medtronic Spinal & Biologies; 2012; 12pp.

Y. Doi et al., "Osteoclastic Responses to Various Calcium Phosphates in Cell Cultures", Journal of Biomedical Materials Research; vol. 47, Issue 3, Dec. 1999; Abstract 3pp.

D.Minh et al., "Synthesis of Calcium Hydroxyapatite From Calcium Carbonate and Different Orthophosphate Sources: A Comparative Study", Materials Science & Engineering: B; vol. 177, Issue 13; Aug. 1, 2012; Abstract 2pp.

D. Bayraktar et al., "Chemical Preparation of Carbonated Calcium Hydroxyapatite Powders at 37° C. in Urea-containing Synthetic Body Fluids", Journal of European Ceramic Society 19; 1999; pp. 2573-2579.

Kandelwal, Himanshu, et al. "Synthesis and Characterization of Hydroxyapatite Powder by Eggshell", Journal of Minerals and Materials Characterization and Engineering, 2016, 4, 119-126, Abstract.

Office Action issued by Korean Patent Office dated May 9, 2021 in corresponding Korean Patent Application No. 10-2018-7031941 corresponding to PCT/US2017/028347. English translation dated Jun. 8, 2021 included.

\* cited by examiner

IMPLANTABLE COMPOSITE CONTAINING CARBONATED HYDROXYAPATITE

BACKGROUND

Autogenous bone is a composite material composed of impure hydroxyapatite, collagen, and a variety of non-collagenous proteins, as well as embedded and adherent cells. Autogenous bone can be processed into an implantable biomaterial, such as an allograft, for example, by removing the cells, leaving behind the extracellular matrix. The processed bone material can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone and may alternatively be processed into soft, moldable, or flowable demineralized bone materials that have the ability to induce a cellular healing response.

The use of bone grafts and bone substitute materials in orthopedic medicine is well known. While bone can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implantable composite site due to stress shielding. Furthermore, most metal implants are permanent and unable to participate in physiological remodeling.

The inorganic component of human bone is primarily composed of calcium, phosphate ions ($Ca^{2+}$, $PO_4^{2-}$, that form the apatite phase), carbonate ions ($CO_3^{2-}$) and small percentages of other ions, such as $Mg^{2+}$ and $Na^+$, for example.

The carbonate renders the bone-like tissue more "dynamic" (that is, stoichiometrically unstable) and thus more easily reabsorbed by osteoclasts.

One of the most widely used bone-like substitutes in today's surgery is represented by synthetic hydroxyapatite (HA), whose formula will be indicated as $Ca_{10}(PO_4)_6(OH)_2$. However, this synthetic hydroxyapatite is not a perfect biomimetic substitute of natural bone tissue and is slowly resorbable. In particular, hydroxyapatite alone can remain in a bone defect for long periods preventing resorption. In contrast, pure tricalcium phosphate (TCP) tends to remodel too quickly to provide sufficient scaffolding for new bone ingrowth and can potentially allow for soft tissue to collapse into the bone defect.

Therefore, there exists a need for formulations or implantable composites that remodel more quickly than pure hydroxyapatite, but do not resorb as quickly as pure tricalcium phosphate.

SUMMARY

An implantable composite including a plurality of resorbable ceramic particles or granules is provided. In certain aspects, the resorbable ceramic particles can include carbonated hydroxyapatite and tricalcium phosphate in a ratio from about 5:95 to about 70:30. In some aspects, the tricalcium phosphate in the ceramic particles of the implantable composite is β tricalcium phosphate. In other embodiments, the plurality of resorbable ceramic particles contain carbonated hydroxyapatite and tricalcium phosphate in a ratio of from about 99:1 to about 1:99 by weight of the osteoconductive implantable composite. In some embodiments, the carbonated hydroxyapatite can be A-type, B-type and/or AB-type substituted. In some embodiments, the implantable composite further comprises autologous bone.

In some embodiments, the resorbable ceramic particles are granules having an average diameter in the range from about 0.4 to about 3.5 mm, and in other embodiments, the average diameter of the resorbable ceramic granules is from about 1.5 to about 3.5 mm.

In various aspects, the resorption rate of the implantable composite increases from about 10% to about 40% when compared to the resorption rate of an implantable composite having resorbable ceramic particles comprising biphasic calcium phosphate including hydroxyapatite and β tricalcium phosphate in a ratio from about 5:95 to about 70:30.

In certain embodiments, the implantable composite can also include a biodegradable polymer which comprises one or more poly(L-lactide-co-D,L-lactide), polyglyconate, poly(arylates), poly(anhydrides), poly(hydroxy acids), polyesters, poly(orthoesters), poly(alkylene oxides), polycarbonates, poly(propylene fumarates), poly(propylene glycol-co fumaric acid), poly(caprolactones), polyamides, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxy-butyrate/valerate copolymers, poly(vinyl pyrrolidone), polycyanoacrylates, polyurethanes, polysaccharides, alginates, polyglycerols, chitosan or combinations thereof. In some aspects, the biodegradable polymer comprises soluble collagen and insoluble collagen in a ratio of about 30:70. In some aspects, the implantable composite comprises glycerol. In other aspects, the implantable composite can include other materials, for example bone-derived material, (e.g., porcine, bovine, human), the bone-derived material comprising non-demineralized bone particles, demineralized bone particles, deorganified bone particles, partially demineralized bone particles, superficially demineralized bone particles, an organic bone particles, or combinations thereof. In other aspects, the implantable composite can include one or more of an initiator, accelerator, catalyst, solvent, wetting agent, lubricating agent, labeling agent, plasticizer, radiopacifier, porogen, bioactive agent, biostatic agent, cell, polynucleotide, protein, pharmaceutical agent or pharmaceutically acceptable excipient.

In various embodiments, the implantable composite can be configured to be moldable after being wetted with a fluid, the fluid comprising water, sodium chloride, Lactated Ringer's solution, blood, marrow, bone marrow aspirate, bone marrow concentrate, or a combination thereof. In some embodiments, the implantable composite can include autologous bone or autograft bone, which can be used as a graft extender.

In other embodiments, provided is an implantable composite configured to fit at or near a bone defect site to promote bone growth, the implantable composite can be a matrix comprising: a biodegradable polymer and a plurality of resorbable ceramic particles, the resorbable ceramic particles comprising carbonated hydroxyapatite and tricalcium phosphate in a ratio from about 5:95 to about 70:30 and having a particle size from about 0.4 to about 3.5 mm.

In certain embodiments, provided is a method of treating a bone in a subject, the method comprising implanting into a bone cavity of a subject in need thereof an implantable composite, the implantable composite comprising a plurality of resorbable ceramic particles and a biodegradable polymer, the resorbable ceramic particles comprising carbonated hydroxyapatite and β tricalcium phosphate in a ratio from about 5:95 to about 70:30. In some embodiments, the step of implanting includes mixing the osteoconductive implantable composite with a fluid comprising water, sodium chloride, Lactated Ringer's solution, blood, marrow, bone marrow aspirate, bone marrow concentrate or a combination thereof. In various aspects, the biodegradable polymer of the implantable composite can include soluble collagen and insoluble collagen, the soluble collagen and insoluble collagen being in a ratio of about 30:70. In some embodiments, the soluble collagen and insoluble collagen can be in a ratio of about 0:100, 1:100, or 1:99. In some embodiments, the implantable composite can be mixed with autologous bone or autograft bone.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound is used herein to refer to a compound or entity that alters, inhibits, activates, or otherwise affects biological or chemical events. For example, bioactive agents may include, but are not limited to, osteoconductive or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In some embodiments, the bioactive agent can form a bond between the composite implant and bone. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin. Bone is also used in the most general sense and includes all types of human or animal bone tissue, including whole bones, bone pieces, bone blocks with attached connective tissues such as ligaments and tendons, as well as ground bone preparations and ground demineralized bone preparations.

Implantable composite is used to refer to a unified combination of two or more distinct materials. The implantable composite may be homogeneous or heterogeneous. For example, an implantable composite may be a combination of bone-derived particles and a polymer; or a combination of a bone substitute material and a polymer. In certain embodiments, the implantable composite has a particular orientation.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, demineralized bone has less than 95% of its original mineral content. In some embodiments, demineralized bone less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "partially demineralized," "surface demineralized," and "fully demineralized." "Partially demineralized" is intended to encompass "surface demineralized."

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone activity refers to the osteoinductive activity of demineralized bone.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium) are also considered within the scope of the current application.

Non-demineralized refers to bone or bone particles, refers to bone or bone-derived material (e.g., particles) that have not been subjected to a demineralization process (i.e., a procedure that totally or partially removes the original inorganic content of bone).

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In some embodiments, the matrix can be a biodegradable depot.

Osteoimplant is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and nonunions, external, and internal fixations, joint reconstructions such as arthrodesis, general arthroplasty, deficit filling, disectomy, laminectomy, anterior cervical and thoracic operations, or spinal fusions.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM is has been shown to promote bone formation in vivo by osteoconductive and osteoinductive processes. The osteoinductive effect of implanted DBM compositions results from the presence of active growth factors present on the isolated collagen-based matrix. These factors include members of the TGF-R, IGF, and BMP protein families. Particular examples of osteoinductive factors include TGF-$\beta$, IGF-1, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

Plasticizer, as used herein, refers to an additive that softens hard polymers or plastics. The plasticizer makes the polymer formable or flexible. Plasticizers are thought to work by embedding themselves between the chains of polymers, spacing them apart, and thus lowering the glass transition temperature. Preferably, the plasticizers used in the implantable composites are non-toxic and biocompatible. In certain embodiments, as the plasticizer diffuses out of the implantable composite osteoimplant the implantable composite loses its formability.

Virus, as used herein, refers to viruses and virus-like particles including enveloped or lipid-coated viruses, and non-enveloped, protein encased viruses. A "virion" is an individual virus entity or particle. As used herein, the term "inactive" means the virion particle is unable to replicate or infect a host cell.

Osteoconductive, as used herein, refers to the ability of a substance to serve as a template or substance along which bone may grow.

Osteogenic, as used herein, refers to materials containing living cells capable of differentiation into bone tissue.

Osteoimplant, as used herein, refers to any implant prepared in accordance with the embodiments described herein and therefore may include expressions such as bone material, bone membrane, bone graft.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.*, 357:219-228, December 1998, incorporated herein by reference.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally, osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Porogen refers to a chemical compound that may be part of the implantable composite and upon implantation or prior to implantation diffuses, dissolves, and/or degrades to leave a pore in the osteoimplant implantable composite. The porogen may be introduced into the implantable composite during manufacture, during preparation of the implantable composite (e.g., in the operating room), or after implantation. The porogen essentially reserves space in the implantable composite while the implantable composite is being molded but once the implantable composite is implanted the porogen diffuses, dissolves, or degrades, thereby inducing porosity into the implantable composite. In this way the porogen provides latent pores. In certain embodiments, the porogen may also be leached out of the implantable composite before implantation. This resulting porosity of the implantable composite generated during manufacture or after implantation (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogen can also be natural or synthetic polymers, oligomers, or monomers that are water soluble or degrade quickly under physiological conditions. Exemplary polymers include polyethylene glycol, poly(vinylpyrrolidone), pullulan, poly(glycolide), poly(lactide), poly(lactide-co-glycolide), other polyesters, and starches.

Porosity refers to the average amount of non-solid space contained in a material (e.g., an implantable composite of the present disclosure). The porosity of an implantable composite can be defined as the ratio of the total volume of the pores (i.e., void volume) in the material to the overall volume of the implantable composite. Porosity may in certain embodiments refer to "latent porosity" wherein pores are only formed upon diffusion, dissolution, or degradation of a material occupying the pores. The pores in such an instance may be formed after implantation.

Remodeling, as used herein, describes the process by which native bone, processed bone allograft, whole bone sections employed as grafts, and other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as hydroxyapatite) are replaced with living bone.

Resorbable, as used herein, refers to a material that exhibits chemical dissolution or is removed by phagocytosis when placed in a mammalian body.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "partially demineralized" as used herein refers to bone-derived elements possessing from about 8 to about 90 weight percent of their original inorganic mineral content. In some embodiments, partially demineralized contains about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 weight percent of their original inorganic mineral content. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

Sterilization, as used herein, refers to an act or process using either physical or chemical means for eliminating or inactivating substantially all viable organisms, especially micro-organisms, viruses and other pathogens, associated with a xenograft or bioprosthetic device. As used herein, "sterilized" includes bone material achieving a sterility assurance level of $10^{-6}$ colony forming unit (CFU), as determined by FDA (Federal Drug Administration) standards.

It is noted that, as used in this specification and the appended claims, the singular forms "a," "an," and "the," include plural referents unless expressly and unequivocally limited to one referent. Thus, for example, reference to "an implant" includes one, two, three or more implants.

Bioactive agent as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

Biodegradable includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells)

infiltrate the components and allow repair of the defect. By "biodegradable" it is meant that the compounds or components will erode or degrade over time due, at least in part, to contact with substances found in the surrounding tissue, fluids or by cellular action. By "bioabsorbabie" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure.

A "therapeutically effective amount" or "effective amount" is such that when administered results in alteration of the biological activity, such as, for example, enhancing bone growth. The dosage administered to a patient can be as single or multiple doses depending upon a variety of factors, including the drug's administered pharmacokinetic properties, the route of administration, patient conditions and characteristics (sex, age, body weight, health, or size), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

The term "implantable" as utilized herein refers to a biocompatible device (e.g., implant) retaining potential for successful placement within a mammal. The expression "implantable device" and expressions of the like import as utilized herein refers to an object implantable through surgery, injection, or other suitable means whose primary function is achieved either through its physical presence or mechanical properties.

Localized delivery includes delivery where one or more drugs are deposited within a tissue, for example, a bone cavity, or in close proximity (within about 0.1 cm, or preferably within about 10 cm, for example) thereto.

Mammal refers to organisms from the taxonomy class "mammalian," including but not limited to humans, other primates such as monkeys, chimpanzees, apes, orangutans and monkeys, rats, mice, rabbits, cats, dogs, pigs, cows, horses, and the like.

Particle refers to pieces of a substance of all shapes, sizes, thickness and configuration such as fibers, threads, narrow strips, thin sheets, clips, shards, etc., that possess regular, irregular or random geometries. It should be understood that some variation in dimension will occur in the production of the particles and particles demonstrating such variability in dimensions are within the scope of the present application. For example, the mineral particles (e.g., ceramic) can be from about 0.5 mm to about 3.5 mm. In some embodiments, the mineral particles can be from about 0.2 mm to about 1.6 mm.

In some embodiments, the implantable composite comprises a matrix. The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable. In other embodiments, the matrix is hydrophilic and absorbs water readily.

In some embodiments, the matrix can be malleable, cohesive, flowable and/or can be shaped into any shape. The term "malleable" includes that the matrix is capable of being converted from a first shape to a second shape by the application of pressure.

The term "cohesive" as used herein means that the putty tends to remain a singular, connected mass upon movement, including the exhibition of the ability to elongate substantially without breaking upon stretching.

The term "moldable" includes that the matrix can be shaped by hand or machine or injected in the target tissue site (e.g., bone defect, fracture, or void) in to a wide variety of configurations. In some embodiments, the matrix can be formed into sheets, blocks, rings, struts, plates, disks, cones, pins, screws, tubes, teeth, bones, portion of bone, wedges, cylinders, threaded cylinders, or the like, as well as more complex geometric configurations.

The terms "treating" and "treatment" when used in connection with a disease or condition refer to executing a protocol that may include osteochondral repair procedure, administering one or more drugs to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the matrix can be used to treat subchondral, osteochondral, hyaline cartilage and/or condyle defects.

The section headings below should not be restricted and can be interchanged with other section headings.

Ceramic Particles

In certain embodiments, the implantable composite includes a plurality of ceramic particles, wherein the ceramic particles comprise biphasic calcium phosphate which comprises, consist essentially of or consist of carbonated hydroxyapatite and tricalcium phosphate in a ratio from about 5:95, 10:90, 15:85, 20:80; 30:70, 35:75, 40:60, 45:55, 50:50, 55:45, 60:40, 65:35 to about 70:30. In some embodiments, the tricalcium phosphate is β tricalcium phosphate. In some embodiments, the ratio of carbonated hydroxyapatite to tricalcium phosphate (CHA:TCP) found in the biphasic calcium phosphate useful in the implantable composite of this disclosure varies from 99:1, 95:5, 90:10, 85:15, 80:20, 75:25, 70:30, 65:35, 60:40, 55:35, 50:50, 45:55, 35:65, 30:70, 25:65, 20:80, 15:85, 10:90, 5:95 to 1:99.

In various embodiments, a high purity mixed AB-type carbonate hydroxyapatite can be produced by the aqueous precipitation in the presence of carbonate ions in a solution of calcium phosphate apatite with a Ca/P molar ratio greater that stoichiometric value of 1.67 for hydroxyapatite as described in Gibson, et al., "Novel synthesis and characterization of an AB-type carbonate substituted hydroxyapatite," *J. Biomed. Mater. Res.*, Mar. 15, 2002, 59 (4):697-708.

In other embodiments, the synthesis of carbonated hydroxyapatite type 13 can be performed by bubbling $CO_2$, as a source of carbonate, into a suspension of $Ca(OH)_2$ and contemporaneously dropping a $H_3PO_4$ solution. The amounts of reagents were chosen in order to respect the Ca/P molar ratio 1.67 of the stoichiometric hydroxyapatite; in this way, a competition for entering in the apatite structure was created between phosphate and carbonate groups as described in Landi et al., "Influence of synthesis and sintering parameters on the characteristics of carbonate apatite," *Biomaterials*, 25, 2004, 1763-1770.

In some embodiments, the particles in the matrix comprise a resorbable ceramic, bone, synthetic degradable polymer, hyaluronic acid, chitosan or combinations thereof. In some embodiments, the particles comprise cortical, cancellous, and/or cortico-cancellous, allogenic, xenogenic or transgenic bone tissue. The bone component can comprise, consist essentially of or consist of fully mineralized bone or partially or fully demineralized bone or combinations thereof. In some embodiments, the mineral particles comprise, consist essentially of or consist of bone powder, demineralized bone powder, porous calcium phosphate ceramics, hydroxyapatite, tricalcium phosphate, bioactive glass or combinations thereof.

In some embodiments, the implantable composite may comprise a resorbable ceramic (e.g., hydroxyapatite, tricalcium phosphate, bioglasses, calcium sulfate) tyrosine-derived polycarbonate poly (DTE-co-DT carbonate), in which the pendant group via the tyrosine an amino acid is either an ethyl ester (DTE) or free carboxylate (DT) or combinations thereof.

In some embodiments, the matrix may contain an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the implantable composite, this will act as a local source of calcium and phosphate to the cells attempting to deposit new bone. The inorganic ceramic also provides compression resistance and load bearing characteristics to the implantable composite.

In some embodiments, the implantable composite can contain demineralized bone material disposed therein. The demineralized bone material can comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the covering may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the implantable composite comprises elongated demineralized bone fibers having an average length to average thickness ratio or aspect ratio of the fibers from about 50:1 to about 1000:1. In overall appearance the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

In some embodiments, the implantable composite comprises elongated demineralized bone fibers and chips. In some embodiments, the implantable composite comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In certain embodiments, the bone graft material that can be placed in the implantable composite described in this disclosure can be demineralized bone material (e.g., fibers, chips, powder, or a combination thereof). In some embodiments, the demineralized bone fibers can be elongated and have an aspect ratio of at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the bone chips can be used and they can be combined with bone fibers, where the chips to fibers ratio is about 90:10, 80:20, 70:30, 60:40, 50:50, 40:60, 30:70, 20:80 and/or 10:90. In various embodiments, a surface demineralized bone chips to fibers ratio is about 90:10, 80:20, 70:30, 60:40, 50:50, 40:60, 30:70, 20:80 and/or 10:90 that can be used in the device. In some embodiments, a surface demineralized chips to fully demineralized fibers ratio is about 90:10, 80:20, 70:30, 60:40, 50:50, 40:60, 30:70, 20:80 and/or 10:90 that can be used in the implantable composite.

In some embodiments, the implantable composite comprises demineralized bone matrix fibers and demineralized bone matrix chips in a 30:60 ratio. In some embodiments, the implantable composite comprises demineralized bone matrix fibers and demineralized bone matrix chips in a ratio of 25:75 to about 75:25 fibers to chips.

In some embodiments, the implantable composite comprises mineral particles that offer compression resistance. In some embodiments, the particles comprise at least 10%, 15%, 20%, 25%, 30%, 35%, 40%, 45%, 50%, 55%, 60%, 65%, 70%, 75%, 80%, 85%, 90%, or 95% by weight of the matrix or composite. In some embodiments, the particles are predominantly any shape (e.g., round, spherical, elongated, powders, chips, fibers, cylinders, etc.). In some embodiments, the matrix or composite comprises mineral particles in an amount of about 0.1 wt % to about 95 wt (4) of the matrix or composite. In some embodiments, the matrix or composite comprises mineral particles in an amount of about 50 wt % to about 80 wt % of the matrix or composite. In some embodiments, the matrix or composite comprises 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, or 79% by weight of the matrix or composite.

In some embodiments, the mineral particles are present in an amount of about 0.1 wt to about 30 wt % of the matrix or composite. In some embodiments, the mineral particles are present in an amount between about 0.01 wt % to about 50 wt % of the matrix or composite. In some embodiments, the mineral particles are present in an amount between about 7.0 wt % to about 50 wt % of the matrix or composite. In some embodiments, the mineral particles are present in an amount of about 0.1 wt % to about 10 wt %, about 10 wt % to about 20 wt %, about 20 wt % to about 30 wt % about 30 wt % to about 40 wt %, or about 40 wt % to about 50 wt %.

In some embodiments, the porosity of the particles comprises from 0 to 50%, or 0 to 90%, in other embodiments, the porosity of the particles comprises 5% to 25%. In some embodiments, the particles are not entangled with each other but contact each other and portions of each particle overlap in the matrix of the implantable composite to provide compression resistance. In some embodiments, at least 50%, 55%, 60%, 65%, 70%, 75%, 80%, 85%, 90%, 95%, or more of the particles overlap each other in the matrix or composite.

In some embodiments, the particles are randomly distributed throughout the matrix of the implantable composite. In other embodiments, the particles are uniformly or evenly distributed throughout the matrix of the implantable composite. In some embodiments, the particles may be dispersed in the matrix or composite using a dispersing agent. In other embodiments, the particles may be stirred in the polymer and the mechanical agitation will distribute the particles in the matrix of the implantable composite until the desired distribution is reached (e.g., random or uniform).

In some embodiments, the matrix of the implantable composite may be seeded with harvested bone cells and/or bone tissue, such as for example, cortical bone, autogenous bone, allogenic bones and/or xenogenic bone. In some embodiments, the matrix of the composite may be seeded with harvested cartilage cells and/or cartilage tissue (e.g., autogenous, allogenic, and/or xenogenic cartilage tissue). For example, before insertion into the target tissue site, the matrix of the implantable composite can be wetted with the graft bone tissue/cells, usually with bone tissue/cells aspirated from the patient, at a ratio of about 3:1, 2:1, 1:1, 1:3 or 1:2 by volume.

The bone tissue/cells are permitted to soak into the matrix of the implantable composite, and the matrix may be kneaded by hand or machine, thereby obtaining a pliable and cohesive consistency that may subsequently be packed into the bone defect. In some embodiments, the matrix of the implantable composite provides a malleable, non-water soluble carrier that permits accurate placement and retention at the implantation site. In some embodiments, the harvested bone and/or cartilage cells can be mixed with a statin and seeded in the interior of the matrix of the implantable composite.

In some embodiments, tissue will infiltrate the matrix of the implantable composite to a degree of about at least 50 percent within about 1 month to about 6 months after implantation of the composite. In some embodiments, about 75 percent of the matrix of the implantable composite will be infiltrated by tissue within about 2-3 months after implantation of the composite. In some embodiments, the composite will be substantially, e.g., about 90 percent or more, submerged in or enveloped by tissue within about 6 months after implantation of the composite. In some embodiments, the matrix of the implantable composite will be completely submerged in or enveloped by tissue within about 9-12 months after implantation.

Biodegradable Polymers

In some embodiments, the implantable composite includes biodegradable polymers. Exemplary biodegradable materials include lactide-glycolide copolymers of any ratio (e.g., 85:15, 40:60, 30:70, 25:75, or 20:80), poly(L-lactide-co-D,L-lactide), polyglyconate, poly(arylates), poly(anhydrides), poly(hydroxy acids), polyesters, poly(ortho esters), poly(alkylene oxides), polycarbonates, polypropylene fumarates), poly(propylene glycol-co fumaric acid), poly (caprolactones), polyamides, polyesters, polyethers, polyureas, polyamines, polyamine acids, polyacetals, poly(orthoesters), poly(pyrolic acid), poly(glaxanone), poly (phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrolidone), biodegradable polycyanoacrylates, biodegradable polyurethanes including glucose-based polyurethanes and lysine-based polyurethanes, and polysaccharides (e.g., chitin, starches, celluloses). In certain embodiments, the polymer used in the implantable composite is poly(lactide-co-glycolide). The ratio of lactide and glycolide units in the polymer may vary. Particularly useful ratios are approximately 45-80% lactide to approximately 44-20% glycolide. In certain embodiments, the ratio is approximately 50% lactide to approximately 50% glycolide. In other certain embodiments, the ratio is approximately 65% lactide to approximately 45% glycolide. In other certain embodiments, the ratio is approximately 60% lactide to approximately 40% glycolide. In other certain embodiments, the ratio is approximately 70% lactide to approximately 30% glycolide. In other certain embodiments, the ratio is approximately 75% lactide to approximately 25% glycolide. In certain embodiments, the ratio is approximately 80% lactide to approximately 20% glycolide. In certain of the above embodiments, lactide is D,L-lactide. In other embodiments, lactide is L-lactide. In certain particular embodiments, RESOMER® 824 (poly-L-lactide-co-glycaide) (Boehringer is used as the polymer in the implantable composite. In certain particular embodiments, RESOMER® 504 (poly-D,L-actide-co-glycolide) (Boehringer Ingelheim) is used as the polymer in the implantable composite. In certain particular embodiments, PURASORB PLG (75/25 poly-L-lactide-co-glycolide) (Purac Biochem) is used as the polymer in the implantable composite. In certain particular embodiments. PURASORB PG (polyglycolide) (Purac Biochem) is used as the polymer in the implantable composite. In certain embodiments, the polymer is PEGylated-poly(lactide-co-glycolide). In certain embodiments, the polymer is PEGylated-poly(lactide). In certain embodiments, the polymer is PEGylated-poly(glycolide). In other embodiments, the polymer is polyurethane. In other embodiments, the polymer is polycaprolactone.

In certain embodiments, the polymer is a copolymer of poly(caprolactone) and poly(lactide). For polyesters such as poly(lactide) and poly(lactide-co-glycolide), the inherent viscosity of the polymer ranges from about 0.4 dL/g to about 5 dl/g. In certain embodiments, the inherent viscosity of the polymer ranges from about 0.6 dl/g to about 2 dl/g. In certain embodiments, the inherent viscosity of the polymer ranges from about 0.6 dl/g to about 3 dL/g. In certain embodiments, the inherent viscosity of the polymer ranges from about 1 dL/g to about 3 dL/g. In certain embodiments, the inherent viscosity of the polymer ranges from about 0.4 dL/g to about 1 dL/g. For poly(caprolactone), the inherent viscosity of the polymer ranges from about 0.5 dL/g to about 1.5 dL/g. In certain embodiments, the inherent viscosity of the poly (caprolactone) ranges from about 1.0 dL/g to about 1.5 dL/g. In certain embodiments, the inherent viscosity of the poly (caprolactone) ranges from about 1.0 dL/g to about 1.2 dL/g. In certain embodiments, the inherent viscosity of the poly (caprolactone) is about 1.08 dL/g.

Natural polymers, including collagen, polysaccharides, agarose, glycosaminoglycans, alginate, chitin, and chitosan, may also be employed. Tyrosine-based polymers, including but not limited to polyarylates and polycarbonates, may also be employed (Pulapura, et al., "Tyrosine-derived polycarbonates: Backbone-modified "pseudo"-poly(arnino acids) designed for biomedical applications," *Biopolymers,* 1992, 32: 411-417; Hooper, et al., "Diphenolic monomers derived from the natural amino acid α-L-tyrosine: an evaluation of peptide coupling techniques," *J. Bioactive and Compatible Polymers,* 1995, 10:327-340, the contents of both of which are incorporated herein by reference). Monomers for tyrosine-based polymers may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, etc. The polymers described in the application entitled "Polyurethanes for Osteoimplants," filed on even date herewith, may also be used in embodiments of the present disclosure. In one embodiment, the degradation products include bioactive materials, biomolecules, small molecules, or other such materials that participate in metabolic processes.

Polymers may be manipulated to adjust their degradation rates. The degradation rates of polymers are well characterized in the literature (see *Handbook of Biodegradable Polymers, Domb,* et al, eds., Harwood Academic Publishers, 1997, the entire contents of which are incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Co-monomers or mixtures of polymers, for example, lactide and glycolide polymers, may be employed to manipulate both degradation rate and mechanical properties.

In some embodiments, the matrix comprises biodegradable polymeric or non-polymeric material. In some embodiments, the matrix may include a biodegradable biopolymer that may provide immediate release, or sustained release of the biologically active material. For example, the biodegradable polymer comprises polyether ether ketone (PEEK). In some embodiments, the matrix may comprise one or more poly (alpha-hydroxy acids), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyroldone, polyamide, oxycellulose, copolymer of glycolic acid and trimethylene carbonate, polyesteramides, polyether ether ketone, polymethylmethacrylate, silicone, hyaluronic acid, chitosan, or combinations thereof.

In some embodiments, the implantable composite may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylactylatnide), PEO-PPO-PEO (pluronics) or combinations thereof. Typically, these types of matrices may need to be removed after a certain amount of time.

In some embodiments, the implantable composite comprises biodegradable polymers comprising wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof. In some embodiments, the biologically active material is encapsulated in a biodegradable polymer.

In some embodiments, the matrix comprises one or more polymers (e.g., PLA, PLGA, etc.) having a MW of from about 15,000 to about 150,000 Da or from about 25,000 to about 100,000 Da.

In some embodiments, the implantable composite comprises at least one biodegradable material in a wt % of from about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 50%, 45%, 35%, 25%, 20%, 15%, 10%, to about 5% based on the total weight of the matrix or the implant. In some embodiments, the biodegradable polymer comprises a range of about 0.1% to about 20% based on the total weight of the matrix or the implant. In some embodiments, the biodegradable polymer comprises a range of about 0.1% to about 15% based on the total weight of the matrix or the implant. In some embodiments, the biodegradable polymer comprises 14%, 13%, 12%, 11%, 9%, 8%, 7%, 6%, or 5% based on the total weight of the matrix or the implant.

In some embodiments, the biodegradable polymer is present in an amount of about 0.01 wt % to about 50 wt % or about 8.0 wt % to about 50 wt % of the matrix. In some embodiments, the biodegradable polymer is present in an amount of about 0.1 wt % to about 10 wt %, about 10 wt % to about 20 wt %, about 20 wt % to about 30 wt %, about 30 wt % to about 40 wt %, or about 40 wt % to about 50 wt %.

Mannitol, trehalose, dextran, mPEG and/or PEG may be used as a plasticizer for the polymer. In some embodiments, the polymer and/or plasticizer may also be coated on the implantable composite to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the biologically active material from the implant. In some embodiments, the range of the coating on the implantable composite ranges from about 5 microns to about 250 microns or 5 microns to about 200 microns to delay release from the implant.

Compression resistance is needed for many tissue engineering applications such as tibial plateau fractures, acetabular defects, long bone comminuted fractures, oral maxillofacial defects, spinal fusions, and cartilage subchondral defects. Compression resistant matrices will help facilitate adequate volumes of newly formed bone.

In some embodiments, the implant is compression resistant where the implant resists reduction in size or an increase in density when a force is applied as compared to implants without the elongated particles disposed in it. In various embodiments, the implant resists compression by at 10%, 15%, 20%, 25%, 30%, 35%, 40%, 45%, 50%, 55%, 60%, 65%, 70%, 75% 80%, 85%, 90%, 95%, or more in one or all directions when a force is applied to the implant.

Those skilled in the art will recognize that this is an exemplary, not a comprehensive, list of polymers appropriate for in vivo applications. Copolymers, mixtures, and adducts of the above polymers may also be used with the implantable composite of this disclosure.

Collagen

In some embodiments, the biodegradable polymer is collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety. Various collagen materials can be used, alone or in combination with other materials.

In some embodiments, the implantable composite includes both soluble and insoluble collagen. In some embodiments, the collagen contains both soluble collagen and insoluble collagen fibers. The soluble collagen and insoluble collagen fibers can first be prepared separately, and then combined. Both the soluble collagen and the insoluble collagen fibers can be derived from a variety of sources, including human, bovine, ovine, piscine, or porcine sources.

Insoluble collagen material for use in this disclosure can be derived from natural tissue sources, (e.g. xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure. Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from DSM Biomedical (Exton. Pa.), which manufactures a fibrous collagen known as Semed F, from bovine hides. Collagen materials derived from bovine tendon are also manufactured by Integra Life Science Holding Corporation (Plainsboro, N.J.). Naturally-derived or recombinant human collagen materials are also suitable for use in the disclosure. Illustratively, recombinant human collagen products are available from Fibrogen, Inc. (San Francisco, Calif.).

The solid particulate collagen incorporated into the implantable composite of this disclosure can be in the form of intact or reconstituted fibers, or randomly-shaped particles, for example. In certain embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, more preferably less than about 3 mm, and advantageously in the range of about 0.5 mm to 2 mm. Such materials can, for example, be obtained by milling or grinding a porous sponge material and sieving the milled or ground material through a screen having openings sized about 6 mm or smaller, desirably about 0.5 mm to about 2 mm. Retch grinders with associated sieves are suitable for these purposes. Other sources of chemically crosslinked, particulate collagen, in fiber, irregular or other shapes, can also be used to significant advantage, and their use is considered to be another aspect of the present disclosure. These crosslinked particulate materials can be provided as starting materials for preparing compositions as disclosed herein, and therefore as incorporated in the device these particles are individually crosslinked. As well, crosslinked solid collagen particles can be used in combination with non-crosslinked collagen in compositions of the disclosure, wherein the non-crosslinked collagen can be solid (insoluble) or soluble collagen, or combinations thereof. Such crosslinked and non-crosslinked collagen mixtures can be used, for example, to modulate the residence time of the collagen portion of the implantable composite compositions in vivo.

Crosslinking of the collagen can be achieved, for example, by chemical reaction, the application of energy such as radiant energy (e.g., UV light or microwave energy), drying and/or heating and dye-mediated photo-oxidation; dehydrothermal treatment; enzymatic treatment or others. In some embodiments, a chemical crosslinking agent is used. Examples of suitable cross-linking agents include those that contain bifunctional or multifunctional reactive groups, and which react with the matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In certain embodiments, the implantable composite includes moldable compositions that include the insoluble collagen and soluble collagen in a ratio of 70:30 of the implantable composite. In other embodiments, such compositions include insoluble collagen fibers at a level of about 0.05 to 0.08 g/cc in the matrix, and soluble collagen at a level of about 0.02 to about 0.05 g/cc in the matrix. In general, the matrix will include insoluble collagen fibers in an amount (percent by weight) that is at least equal to or greater than the amount of soluble collagen, to contribute beneficially to the desired handling and implant properties of the matrix material. In some embodiments, the collagen of the implantable composite will include insoluble collagen fibers and soluble collagen present in a weight ratio of about 80:20, 75:25, 70:30, 65:35 to about 60:40. In other embodiments, the matrix may include the insoluble collagen fibers and soluble collagen in a weight ratio of about 75:25 to about 65:35, and in one specific embodiment about 70:30.

The biodegradable polymer will exhibit dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g. poly (lactide-co-glycolide), polyanhydrides) may be used. Alternatively, a combination of hydrophilic and hydrophobic polymers may be used in the bone graft composition of the disclosure.

Exemplary materials may include biopolymers and synthetic polymers such as human skin, human hair, bone, collagen, fat, thin cross-linked sheets containing fibers and/or fibers and chips, polyethylene glycol (PEG), chitosan, alginate sheets, cellulose sheets, hyaluronic acid sheet, as well as copolymer blends of poly (lactide-co-glycolide) PLGA.

In some embodiments, the particles disclosed herein can also include other biocompatible and bioresorbable substances. These materials may include, for example, natural polymers such as proteins and polypeptides, glycosaminoglycans, proteoglycans, elastin, hyaluronic acid, dermatan sulfate, gelatin, or mixtures or implantable composites thereof. Synthetic polymers may also be incorporated into the bone graft implantable composites. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, polypropylene furnarate), polyethylene terephthalate), polybutylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers.

The biodegradable polymer may have a molecular weight of from about 1,000 to about 30,000 Daltons (Da). In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the biodegradable polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

Exemplary collagen particles can be obtained from various collagen sources including human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is porous.

Proportions of the polymer may be adjusted within reasonably wide ranges depending upon the properties desired and the clinical applications required. The concentration with respect to the ceramics may be dependent on the nature of the polymer as well as the amount of DBM. In some embodiments, the concentration of the polymer may be from about 3 to about 60 weight percent. In some embodiments, the concentration of the polymer may be about 2% 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to about 40 weight percent. In some embodiments, the polymer is collagen present in an amount from about 2 to about 40 weight percent. In some embodiments, the ceramic granules of the implantable composite is from about 98%, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60 weight percent. It is well within the ability of the skilled artisan to determine the optimal amount of biodegradable polymer without undue experimentation.

Proportions of the collagen may be adjusted within reasonably wide ranges depending upon the properties desired and the clinical applications required. In some embodiments, more than 40 weight percent of the implantable composite is collagen.

In some embodiments, the one or more biodegradable polymers comprises collagen in an amount of 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 2:1.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0% w/w, w/v or v/v of the matrix the remaining comprising ceramic granules containing carbonated hydroxyapatite and tricalcium phosphate in a ratio from about 10:90, 15:85, 20:60, 25:75, 30:70, 35:65, 40:60, 45:55, 50:50, 55:45, 60:40, 65:45 to about 70:30. In some embodiments, the biodegradable polymer is present in an amount of about 0.1 wt to about 20 wt % of the matrix. In some embodiments, the biodegradable polymer is present in an amount between about 0.01 wt % to about 50 wt %, about 8.0 wt % to about 20 wt % or about 8.0 wt % to about 13 wt % of the matrix. In some embodiments, the biodegradable polymer is present in an amount of about 0.1 wt % to about 10 wt %, about 10 wt % to about 20 wt %, about 20 wt % to about 30 wt %, or about 30 wt % to about 40 wt %. As a result of using carbonate hydroxyapatite and tricalcium phosphate in the biphasic calcium phosphate of the implantable composites of this disclosure the chances of the apatite component persisting in the body longer than necessary are reduced. Based on the ratio of carbonated hydroxyapatite and tricalcium phosphate present in the biphasic calcium phosphate in the ratios described above, it is possible to tailor the overall resorption rate of the resulting implantable composite. In particular, it has been unexpectedly found that the resorption of the implantable composites containing carbonated hydroxyapatite increases from about 10%, 15, 20, 30, 35 to about 40% when compared to the resorption of an implantable composite having ceramic particles comprising hydroxyapatite and tricalcium phosphate in the same ratio from about 10:90 to about 70:30.

Exemplary Composite Implants

| Biphasic CHA/TCP in wt % | Biodegradable Polymer (e.g., collagen) in wt. % |
|---|---|
| 98% | 2% |
| 96.5% | 3.5% |
| 80% | 20% |
| 60% | 40% |

Additional Components

The implantable composite can also include other components. For example, the implantable composite may further include one or more of an initiator, accelerator, catalyst, solvent, wetting agent, lubricating agent, labeling agent, plasticizer, radiopacifier, porogen, bioactive agent, biostatic agent, cell, polynucleotide, protein (e.g., bone morphogenic protein, cytokine, growth factor, angiogenic factor), pharmaceutical agent (e.g., anti-inflammatory agent, analgesic, or antibiotic), and pharmaceutically acceptable excipient. In certain embodiments, the implantable composite includes a plasticizer that softens the implantable composite making it more pliable. Exemplary plasticizer include glycerol and polyethylene glycol) (PEG) (e.g., PEG 8000, PEG 6000, PEG 4000). In certain embodiments, the polymer component of the implantable composite includes PEG blended, grafted, or co-polymerized with the polymer.

Additional materials may be included in the implantable composite. The additional material may be biologically active or inert. Additional materials may also be added to the implantable composite to improve its chemical, mechanical, or biophysical properties. Additional materials may also be added to improve the handling or storage of the implantable composite (e.g., a preservative). Those of skill in this art will appreciate the myriad of different components that may be included in the implantable composite.

Additional components of the implantable composite can be any type of chemical compound including proteins, peptides, polynucleotides (e.g., vectors, plasmids, cosmids, artificial chromosomes), lipids, carbohydrates, organic molecules, small molecules, organometallic compounds, metals, ceramics, or polymers. Living cells, tissue samples, or viruses may also be added to the implantable composites. In certain embodiments, the additional material comprises cells, which may optionally be genetically engineered. For example, the cells may be engineered to produce a specific growth factor, chemotactic factor, osteogenic factor, and the like. In certain embodiments, the cells may be engineered to produce a polynucleotide such as a siRNA, shRNA, RNAi, or microRNA. The cell may include a plasmid, or other extra-chromosomal piece of DNA. In certain embodiments, a recombinant construct is integrated into the genome of the cell. In certain embodiments, the additional material comprises a virus. Again, the virus may be genetically engineered. Tissues such as bone marrow and bone samples may be combined with the implantable composite of polymer and bone-derived particles. The implantable composite may include additional calcium-based ceramics such as calcium phosphate and calcium carbonate. In certain embodiments, non-biologically active materials are incorporated into the implantable composite. For example, labeling agents such as radiopaque, luminescent, or magnetically active particles may be attached to the bone-derived particles using silane chemistry or other coupling agents, for example zirconates and titanates, or mixed into the polymer, as described herein. Alternatively, or in addition, poly (ethylene glycol) (PEG) may be attached to the bone particles. Biologically active molecules, for example, small molecules, bioactive agents, and biomolecules such as lipids may be linked to the particles through silane SAMs or using a polysialic acid linker (see, for example, U.S. Pat. No. 5,846,951; incorporated herein by reference).

Plasticizer

The implantable composite may also include one or more other components such as a plasticizer. Plasticizer are typically compounds added to polymers or plastics to soften them or make them more pliable. Plasticizers soften, make workable, or otherwise improve the handling properties of a polymer or implantable composite. Plasticizers also allow the implantable composite to be moldable at a lower temperature, thereby avoiding heat induced tissue necrosis during implantation. The plasticizer may evaporate or otherwise diffuse out of the implantable composite over time, thereby allowing the implantable composite to harden or set. Plasticizers are thought to work by embedding themselves between the chains of polymers. This forces the polymer chains apart and thus lowers the glass transition temperature of the polymer. Typically, the more plasticizer that is added, the more flexible the resulting polymer or implantable composite will be.

In certain embodiments, the plasticizer is based on an ester of a polycarboxylic acid with linear or branched aliphatic alcohols of moderate chain length. For example, some plasticizers are adipate-based. Examples of adipate-based pasticizers include bis(2-ethylhexypadipate (DOA), dimethyl adipate (DMAD), trionomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), and trimethylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl) phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-ethylhexyl) trimellitate (TEHTM-MG), tri-(n-octyl,n-decyl) trimellitate (ATM), tri-(heptyl,nonyl) trimellitate (LTM), n-octyl trimellitate (OTM)), benzoates, epoxidized vegetable oils, sulfonamides (e.g., N-ethyl toluene sulfonamide (ETSA), N-(2-hydroxypropypbenzene sulfonamide (HP BSA), N-(n-butyl)butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in Handbook of Plasticizers (G. Wypych, Ed., ChemTec Publishing, 2004), which is incorporated herein by reference. In certain embodiments, other polymers are added to the implantable composite as plasticizers. In certain particular embodiments, polymers with the same chemical structure as those used in the implantable composite are used but with lower molecular weights to soften the overall implantable composite. In certain embodiments, oligomers or monomers of the polymers used in the implantable composite are used as plasticizers. In other embodiments, different polymers with lower melting points and/or lower viscosities than those of the polymer component of the implantable composite are used. In certain embodiments, oligomers or monomers of polymers different from those used in the implantable composite are used as plasticizers. In certain embodiments, the polymer used as a plasticizer is polyethylene glycol) (PEG). The PEG used as a plasticizer is typically a low molecular weight PEG such as those having an average molecular weight of 1000 to 10000 g/mol, preferably from 4000 to 8000 g/mol. In certain embodiments, PEG 4000 is used in the implantable composite. In certain embodiments, PEG 5000 is used in the implantable composite. In certain embodiments, PEG 6000 is used in the implantable composite. In certain embodiments, PEG 7000 is used in the implantable composite. In certain embodiments, PEG 8000 is used in the implantable composite. The plasticizer (PEG) is particularly useful in making more moldable implantable composites that include poly(lactide), poly(D,L-lactide), poly(lactide-co-glycolide), poly(D,L-lactide-co-glycolide), or poly(caprolactone). In certain embodiments, PEG is grafted onto a polymer of the implantable composite or is co-polymerized with a polymer of the implantable composite.

Plasticizer may comprise 1-40% of the implantable composite by weight. In certain embodiments, the plasticizer is 10-30% by weight. In certain embodiments, the plasticizer is approximately 10% by weight. In certain embodiments, the plasticizer is approximately 15% by weight. In certain embodiments, the plasticizer is approximately 20% by weight. In certain embodiments, the plasticizer is approximately 25% by weight. In certain embodiments, the plasticizer is approximately 30% by weight. In certain embodiments, the plasticizer is approximately 33% by weight. In certain embodiments, the plasticizer is approximately 40% by weight. In certain embodiments, a plasticizer is not used in the implantable composite. For example, in some polycaprolactone-containing implantable composites, a plasticizer is not used.

Porogen

In certain embodiments, the implantable composite includes a porogen that diffuses, dissolves, and/or degrades after implantation of the implantable composite leaving a pore. The porogen may be a gas (e.g., carbon dioxide, nitrogen), liquid (e.g., water), or solid (e.g., crystalline salt). The porogen may be a water-soluble chemical compound such as a carbohydrate (e.g., poly(dextrose), dextran), salt, polymer (e.g., polyvinyl pyrrolidone), protein (e.g., gelatin), pharmaceutical agent (e.g., antibiotics), or a small molecule.

The implantable composites of the present disclosure can exhibit high degrees of porosity over a wide range of effective pore sizes. Thus, implantable composites of the present disclosure may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the implantable composite has a porosity of at least about 30%. For example, in certain embodiments, the implantable composite has a porosity of more than about 50%, more than about 60%, more than about 70%, more than about 80%, or more than about 90%. Advantages of a highly porous implantable composite over less porous or non-porous implantable composite include, but are not limited to, more extensive cellular and tissue in-growth into the implantable composite, more continuous supply of nutrients, more thorough infiltration of therapeutics, and enhanced revascularization, allowing bone growth and repair to take place more efficiently. Furthermore, in certain embodiments, the porosity of the implantable composite may be used to load the implantable composite with biologically active agents such as drugs, small molecules, cells, peptides, polynucleotides, growth factors, osteogenic factors, for delivery at the implantable composite site. Porosity may also render certain implantable composites of the present disclosure compressible.

In certain particular embodiments, the pores of the implantable composite are preferably over 100 microns wide for the invasion of cells and bony in-growth. Klaitwatter et al. "Application of porous ceramics for the attachment of load bearing orthopedic applications" *J. Biomed. Mater. Res. Symp.* 2:161, 1971; each of which is incorporated herein by reference. In certain embodiments, the pore size ranges from approximately 50 microns to approximately 500 microns, preferably from approximately 100 microns to approximately 250 microns.

The porosity of the implantable composite may be accomplished using any means known in the art. Exemplary methods of creating porosity in an implantable composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al. *Tissue Engineering* 8(1):43-52, 2002; incorporated herein by reference). For a review, see Karageorgiou et al, *Biomaterials* 26:5474-5491, 2005; incorporated herein by reference. The porosity may be a feature of the implantable composite during manufacture or before implantation, or the porosity may only be available after implantation. For example, the implanted implantable composite may include latent pores. These latent pores may arise from including porogens in the implantable composite.

The porogen may be any chemical compound that will reserve a space within the implantable composite while the implantable composite is being molded and will diffuse, dissolve, and/or degrade prior to or after implantation leaving a pore in the implantable composite. Porogens preferably have the property of not being appreciably changed in shape and/or size during the procedure to make the implantable composite moldable. For example, the porogen should retain its shape during the heating of the implantable composite to make it moldable. Therefore, the porogen preferably does not melt upon heating of the implantable composite to make it moldable. In certain embodiments, the porogen has a melting point greater than about 60° C., greater than about 70° C., greater than about 80° C., greater than about 85° C., or greater than about 90° C.

Porogens may be of any shape or size. The porogen may be spheroidal, cuboidal, rectangular, elongated, tubular, fibrous, disc-shaped, platelet-shaped, polygonal, etc. In certain embodiments, the porogen is granular with a diameter ranging from approximately 100 microns to approximately 800 microns. In certain embodiments, the porogen is elongated, tubular, or fibrous. Such porogens provide increased connectivity of the pores of the implantable composite and/or also allow for a lesser percentage of the porogen in the implantable composite. The amount of the porogen may vary in the implantable composite from 1% to 80% by weight. In certain embodiments, the plasticizer makes up from about 5% to about 80% by weight of the implantable composite. In certain embodiments, the plasticizer makes up from about 10% to about 50% by weight of the implantable composite. Pores in the implantable composite are thought to improve the osteoinductivity or osteoconductivity of the implantable composite by providing holes for cells such as osteoblasts, osteoclasts, fibroblasts, cells of the osteoblast lineage, stem cells, etc. The pores provide the implantable composite with biological in growth capacity. Pores in the implantable composite may also provide for easier degradation of the implantable composite as bone is formed and/or remodeled. Preferably, the porogen is biocompatible.

The porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). The gaseous or liquid porogen may diffuse out of the implantable composite before or after implantation thereby providing pores for biological in-growth. Solid porogens may be crystalline or amorphous. Examples of possible solid porogens include water soluble compounds. In certain embodiments, the water soluble compound has a solubility of greater than 10 g per 100 mL water at 25° C. In certain embodiments, the water soluble compound has a solubility of greater than 25 g per 100 mL water at 25° C. In certain embodiments, the water soluble compound has a solubility of greater than 50 g per 100 mL water at 25° C. In certain embodiments, the water soluble compound has a solubility of greater than 75 g per 100 mL water at 25° C. In certain embodiments, the water soluble compound has a solubility of greater than 100 g per 100 mL water at 25° C. Examples of porogens include carbohydrates (e.g., sorbitol, dextran (poly(dextrose)), starch), salts, sugar alcohols, natural polymers, synthetic polymers, and small molecules.

In certain embodiments, carbohydrates are used as porogens in the implantable composites. The carbohydrate may be a monosaccharide, disaccharide, or polysaccharide. The carbohydrate may be a natural or synthetic carbohydrate. Preferably, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc. In certain embodiments, the polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as the perogen in the implantable composite. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the implantable composite. Dextran may be about 15% by weight to about 30% by weight of the implantable composite. In certain embodiments, dextran is about 15% by weight, 20% by weight, 25% by weight, or 30% by weight. Higher and lower percentages of dextran may also be used. Once the implantable composite with the dextran as a porogen is implanted into a subject, the dextran dissolves away very quickly. Within approximately 24 hours, substantially all of the dextran is out of the implantable composite leaving behind pores in the implantable composite. An advantage of using dextran in the implantable composite is that dextran exhibits a hemostatic property in the extravascular space. Therefore, dextran in an implantable composite can decrease bleeding at or near the site of implantation.

Small molecules including pharmaceutical agents may also be used as porogens in the implantable composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, the porogen is poly(vinyl pyrrolidone) or a derivative thereof. Plasticizers that are removed faster than the surrounding implantable composite can also be considered porogens.

In certain embodiments, the implantable composite may include a wetting or lubricating agent. Suitable wetting agents include water, organic protic solvents, organic non-protic solvents, aqueous solutions such as physiological saline, concentrated saline solutions, sugar solutions, ionic solutions of any kind, and liquid polyhydroxy compounds such as glycerol, polyethylene glycol (PEG), polyvinyl alcohol (PVA), and glycerol esters, and mixtures of any of these. Biological fluids may also be used as wetting or lubricating agents. Examples of biological fluids that may be used with the implantable composites include blood, lymph, plasma, serum, or marrow. Lubricating agents may include, for example, polyethylene glycol, which can be combined with the polymer and other components to reduce viscosity or even coated on the walls of the delivery device. Alternatively or in addition, the particulate material may be coated with a polymer by sputtering or other techniques known to those skilled in the art.

Biologically Active Molecules

Additionally, implantable composites of the present disclosure may contain one or more biologically active molecules, including biomolecules, small molecules, and bioactive agents, to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

In certain embodiments, the implantable composite include antibiotics. The antibiotics may be bacteriocidal or bacteriostatic. Other anti-microbial agents may also be included in the implantable composite. For example, antiviral agents, anti-protazoal agents, anti-parasitic agents, etc. may be included in the implantable composite. Other suitable biostaticibiocidal agents include antibiotics, povidone, sugars, and mixtures thereof.

Biologically active materials, including biomolecules, small molecules, and bioactive agents may also be combined with the polymer and particles to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in the implantable composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetration enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the implantable composite and/or development of new tissue (e.g., bone). RNAi or other technologies may also be used to reduce the production of various factors.

To enhance biodegradation in vivo, the implantable composites of the present disclosure can also include different enzymes. Examples of suitable enzymes or similar reagents are proteases or hydrolases with ester-hydrolyzing capabilities. Such enzymes include, but are not limited to, proteinase K, bronielaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

These materials need not be covalently bonded to a component of the implantable composite. A material may be selectively distributed on or near the surface of the implantable composite using the layering techniques described above. While the surface of the implantable composite will be mixed somewhat as the implantable composite is manipulated in The implantable composite site, the thickness of the surface layer will ensure that at least a portion of the surface layer of the implantable composite remains at the surface of the implant. Alternatively or in addition, biologically active components may be covalently linked to the bone particles before combination with the polymer. For example, silane coupling agents having amine, carboxyl, hydroxyl, or mercapto groups may be attached to the bone particles through the silane and then to reactive groups on a biomolecule, small molecule, or bioactive agent.

The implantable composite may also be seeded with cells. In certain embodiments, a patient's own cells are obtained and used in the implantable composite. Certain types of cells (e.g., osteoblasts, fibroblasts, stem cells, cells of the osteoblast lineage, etc.) may be selected for use in the implantable composite. The cells may be harvested from marrow, blood, fat, bone, muscle, connective tissue, skin, or other tissues or organs. In certain embodiments, a patient's own cells may be harvested, optionally selected, expanded, and used in the implantable composite. In other embodiments, a patient's cells may be harvested, selected without expansion, and used in the implantable composite. Alternatively, exogenous cells may be employed. Exemplary cells for use with the current application include mesenchymal stem cells and connective tissue cells, including osteoblasts, osteoclasts, fibroblasts, preosteoblasts, and partially differentiated cells of the osteoblast lineage. The cells may be genetically engineered. For example, the cells may be engineered to produce a bone morphogenic protein.

In embodiments where the polymer component becomes formable when heated, the heat absorbed by particles in the implantable composite may increase the cooling time of the implantable composite, extending the time available to form the implantable composite into an implant. Depending on the relative heat capacities of the particle and the polymer components and the size of the particles, the particles may continue to release heat into the surrounding polymer after the time when the polymer alone would have cooled. The size and density distribution of particles within the implantable composite may be optimized to adjust the amount of heat released into portions of an osteoimplant during and after implantation.

Implants and Uses

In some embodiments the implantable composite comprises resorbable ceramic particles and collagen or any other biodegradable polymer in a ratio from about 98:2, 95:5, 90:10, 85:15, 80:20, 75:35, 70:30, 65:35, and 60:40 by % weight. In other embodiments, the implantable composite does not contain any collagen, instead it comprises, consists essentially of or consists of granules of resorbable ceramic.

In some embodiments, the implantable composite comprises a matrix that provides a tissue scaffold for cells to guide the process of tissue formation in vivo in three dimensions. In some embodiments, the implantable composite provides a porous scaffold to promote bone ingrowth. The morphology of the matrix guides cell migration and cells are able to migrate into or over the matrix. The cells then are able to proliferate and synthesize new tissue and form bone and/or cartilage. In some embodiments, one or more tissue matrices are stacked on one another.

In some embodiments, the implantable composite is in a dry cohesive mass. In some embodiments, the implantable composite comprises a cohesive mass of a biodegradable polymer, mineral particles and a biologically active material. The biodegradable polymer, mineral particles and biologically active material comprise fibers, chips or particles which form a coherent mass without any additional carrier. In some embodiments, the fibers, chips or particles are processed in such a way to provide for cohesion between biodegradable polymer, mineral particles and a biologically active material without additional containment or binding agents. In some embodiments, for example, the biodegradable polymer may be milled to create curled fibers. The fibers and particles become physically entangled by surface to surface interactions between adjacent fibers, chips and/or particles. In some embodiments, the entanglement/interaction of the fibers, chips and/or particles is responsible for the cohesiveness of the implantable composite prior to being wetted with a fluid. Thus, in some embodiments, the implantable composite comprises fibers, chips and/or particles having a size and shape that provides for increased surface area and the ability to mechanically interlock with one another to form a coherent mass.

The dried implant material comprises a porous body that includes granules having an average particle diameter of about 0.4 mm to about 5.0 mm homogenously mixed with a biodegradable polymer. In some embodiments, the granules have an average particle size of about 0.5 mm, 0.6, 0.7, 0.8, 0.9, 1.0. 1.1, 1.2, 1.3, 1.4, 1.5 to about 1.6 mm. In some embodiments, the mineral particles have an average particle size of about 1.5 mm, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 mm to about 3.5 mm.

In some embodiment, the mineral granules (e.g., tricalcium phosphate:carbonated hydroxyapatite) can be homogenously disposed throughout the matrix at a particle size of from about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 071, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1.0, 1.25, 1.4, 1.5, 1.6, 1.7, 1.8, 1.9, 2.0, 2.25, 2.50, 2.75, 3.00, 3.25, to about 3.5 mm. These particles can be in the form of granules, chips, fibers or a combination thereof.

In various embodiments, the particle size distribution of the biodegradable polymer may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, the one or more biologically active materials may for example have an average particle size of from about 2.2 to about 10 microns. In some embodiments the biologically active material particles have a minimum average particle size of about 2.2 microns, or about 2.5 microns, or about 3 microns, or about 4 microns. The particles also may have a maximum average particle size of about 10 microns, or about 8 microns, or about 7 microns, or about 5 microns. In some embodiments, the biologically active material has a particle size from about 5 to 30 micrometers, or about 2 microns to about 20 microns, or from 30 microns to 100 microns, however, in various embodiments, ranges from about 1 micron to 250 microns may be used. In some embodiments, the biologically active material has a particle size of about 0.1 nm to about 1 micron to provide enhanced dissolution and quicker release of from the implant. In some embodiments, the biologically active material is in nanoparticle form and from about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 nm in diameter.

In some embodiments, the biologically active material includes a particle size of about 0.1 mm to about 5 mm to lengthen the release duration from the implantable composite by slowing down biologically active material dissolution rate which might modulate bone formation. Moreover, the biologically active material particles may have a monophasic distribution. Additionally, in some embodiments, it may be preferable to have a water-soluble biologically active material in order to produce an acute anti-inflammatory/analgesic effect that the implantable composite is not providing.

In various embodiments, the biologically active material is in the form of a solvate, hydrate or a pharmaceutically acceptable salt. The biologically active material may alternatively be crystallized in an amorphous form. In some embodiments, the biologically active material is in the form of a monohydrate. In some embodiments, the biologically active material may be in amorphous form. In various embodiments, the implantable composite comprises biologically active material and a biodegradable polymer in amorphous, crystalline or semicrystalline form; where the crystalline form may include polymorphs, solvates or hydrates.

In some embodiments, the biologically active material can be loaded to the matrix in highly concentrated amounts. For example, in some embodiments, the biologically active material is loaded into the matrix in an amount of at least 500 mg/cc. In some embodiments, the biologically active material is added to the matrix in an amount of about 1 mg/cc to about 1 g/cc, from about 100 mg/cc to about 1 g/cc, from about 500 mg/cc to about 900 mg/cc, or from about 600 mg/cc to about 800 mg/cc. In other embodiments, the biologically active material is added to the matrix in an amount of about 500 mg/cc to about 600 mg/cc, about 600 mg/cc to about 700 mg/cc, about 700 mg/cc to about 800 mg/cc, about 800 mg/cc to about 900 mg/cc, or about 900 mg/cc to about 1 g/cc. In some embodiments, the biologically active material is loaded into the matrix in an amount of about 134 mg/cc.

In some embodiments, the biologically active material comprises a range of about 5.0 wt % to about 45 wt % based on the total weight of the matrix or the implantable composite prior to or after being wetted. In some embodiments, the implantable composite comprises at least one biodegradable material in a wt % of about 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, or 44% based on the total weight of the matrix or the implant.

In some embodiments, the matrix containing the biologically active material may have a burst release surface that releases about 10%, 15%, 20%, 25%, 30%, 35%, 45%, to about 50% of the biologically active material over 24 or 48 hours.

In some embodiments, a high concentration of the biologically active material can be loaded into the matrix and comprise from about 2.0 wt % to about 90 wt % of the matrix. In some embodiments, the biologically active material can be loaded into the matrix in an amount from about 35 wt % to about 80 wt % or about 50 wt % to about 90 wt % of the matrix. In some embodiments, the biologically active material can be loaded into the matrix in an amount of about 20 wt % to about 30 wt %, about 30 wt % to about 40 wt %, about 40 wt % to about 50 wt %, about 50 wt % to about 60 wt %, about 60 wt % to about 70 wt %, about 70 wt % to about 80 wt %, about 80 wt (4) to about 90 wt %, or about 90 wt % to about 99 wt %. In some embodiments, the biologically active material can be loaded into the matrix in an amount of 20, 25, 30, 35, 40, 45, 50, 55, 60, 65, 70, 75, 80, 85, 90, or 95 wt % of the matrix.

In some embodiments, the matrix releases the biologically active material over a period of 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months. In some embodiments, bone growth will be observed over a period of at least 14 days, for example, 14-90 days, 14-30 days, 14-60 days, 21-90 days, 21-180 days, 14-210 days, or 14 days to 6 months.

In some embodiments, the implantable composite is wetted to form a malleable matrix. The malleable matrix is configured to be moldable to any desired shape to fit a bone defect site. In some embodiments, the malleable implant may be molded to fit into a surgical site, such as a bone defect site. The shape of the matrix may be tailored to the site at which it is to be situated. For example, it may be in the shape of a morsel, a plug, a pin, a peg, a cylinder, a block, a wedge, a sheet, or a strip. The term "shape" refers to a determined or regular form or configuration in contrast to an indeterminate or vague form or configuration (as in the case of a lump or other solid mass of no special form) and is characteristic of such materials as sheets, plates, disks, cores, tubes, wedges, cylinders, or strips. This includes forms ranging from regular, geometric shapes to irregular, angled, or non-geometric shapes, or combinations of features having any of these characteristics. In some embodiments, the implantable composite is malleable, like a putty or paste prior to being implanted into a surgical site. In such embodiments, a medical practitioner may mold the implantable composite to a desired shape and allow the implantable composite to cure or dry prior to implantation. In some embodiments, the implantable composite is malleable in vivo. In such embodiments, a medical practitioner may mold the implantable composite directly into a bone defect site. The implantable composite is malleable and configured to be pressed into a bone defect site to fill out all crevices in a bone defect site. In some embodiments, the implantable composite is malleable when wetted and is configured to remain malleable while in contact with a bone defect site.

In some embodiments, the malleable matrix of the implantable composite can be formed to fit into the void space of an interbody cage or around the outside of the cage in the intervertebral space.

The dry, coherent mass may be wetted or hydrated with a variety of fluids to form a malleable and moldable implant. In some embodiments, the matrix is wetted with sterile water, physiological saline, sodium chloride, dextrose, Lactated Ringer's solution, phosphate buffered saline (PBS), blood, bone marrow aspirate, bone marrow fractions or a combination thereof. The amount of fluid that the matrix can be wetted with includes from about 0.25, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 to about 50.0 mls.

In some embodiments, the implantable composite is hydrated with hyaluronic acid, cellulose ethers (such as carboxymethyl cellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma. After hydrating, the implantable composite becomes a putty or a paste or a strip that can be molded into a predetermined shape or administered to a bone defect and manipulated to conform to the bone defect in such a manner that will promote healing. For example, the composition may be hydrated with about 2 ml of saline blood per 2.5 g of combined DBM and periosteal powder.

In some embodiments, the implantable composite comprises a porous matrix configured to allow influx of at least bone and/or cartilage cells therein. In some embodiments, the matrix is also configured to release an active agent, such as a biologically active material. By "porous," it is meant that the matrix has a plurality of pores. The pores of the matrix are a size large enough to allow influx of blood, other bodily fluid, and progenitor and/or bone and/or cartilage cells into the interior to guide the process of tissue formation in vivo in three dimensions.

In some embodiments, the matrix of the implantable composite comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix of the implantable composite has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue.

In some embodiments, a biologically active material can be administered in an implant that is solid or in semi-solid form. The solid or semi-solid form of the device may have a pre-dosed viscosity in the range of about 1 to about 2000 centipoise (cps), 1 to about 200 cps, or 1 to about 100 cps. In various embodiments, the semi-solid or solid implant may comprise a biodegradable polymer having a molecular weight (MW), as shown by the inherent viscosity, from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 16 dL/g, about 1.5 to about 1:7 dL/g, about 1.6 to about 1.8 dL/g, about 1.7 to about 1.9 dL/g, or about 1.8 to about 2.1 dL/g.

In some embodiments, the matrix has a modulus of elasticity in the range of about $1 \times 10^2$ to about $6 \times 10^5$ dyn/cm$^2$, or $2 \times 10^4$ to about $5 \times 10^5$ dyn/cm$^2$, or $5 \times 10^4$ to about $5 \times 10^5$ dyn/cm$^2$. In some embodiments, the matrix is in the form of a solid or semi-solid.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect). In some embodiments, at the time of surgery, the matrix can be soaked with a biologically active material and molded by the surgeon to the desired shape to fit the tissue or bone defect.

In some embodiments, the porous interior can hold the biologically active material within the matrix and because the interior is porous, the biologically active material is evenly distributed throughout the matrix when biologically active material is incorporated into the matrix, as discussed herein.

In some embodiments, biologically active material will be held within the interior of the matrix of the implantable composite and released into the environment surrounding the matrix (e.g., bone defect, osteochondral defect, etc.) as the matrix degrades over time.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable and cohesive consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the biologically active material and seeded in the interior of the matrix.

Method of Treating

In some embodiments, the implantable composite comprises a biodegradable polymer, mineral particles and a biologically active material, such as, for example, biologically active material, to promote osteogenesis. In use, biologically active material provides therapeutic treatment for bone conditions. Biologically active material facilitates bone formation, osteoblastic differentiation, osteomorphogenesis and/or osteoproliferation. Treatment can be administered to treat open fractures and fractures at high risk of non-union, and in subjects with spinal disorders. That is, biologically active material can induce spinal fusion and may help treat degenerative disc disease or arthritis affecting the lumbar or cervical vertebrae.

In some embodiments, the implantable composite can be combined with autologous bone and then wetted with a fluid, for example, sterile water, sodium chloride, Lactated Ringer's solution, blood, marrow, bone marrow aspirate, bone marrow concentrate or a combination thereof. In other embodiments, the implantable composite is administered by first wetting the matrix to impart malleability and moldability properties to the implant. The implantable composite can be molded to different sizes, shapes and configurations. There are several factors that can be taken into consideration in determining the size, shape and configuration of the implant. For example, both the size and shape may allow for ease in positioning the implantable composite at the target tissue site that is selected as the implantation. In addition, the shape and size of the system should be selected so as to minimize or prevent the implantable composite from moving after implantation. In various embodiments, the implantable composite can be shaped like a rod or a flat surface such as a film or sheet (e.g., ribbon-like) or a strip. Flexibility may be a consideration so as to facilitate placement of the device.

Mesenchymal stem cells treated with certain biologically active material can have increased osteoblast differentiation. Thus, in some embodiments, a matrix comprising biologically active material may be implanted into a spinal site with mesenchymal stem cells to induce bone growth through osteoblast differentiation. Periosteum tissue is one tissue type that is involved early during normal bone fracture repair process and can recruit various cell types (e.g., mesenchymal stem cells) and bone growth factors necessary for bone fracture repair. Thus, in some embodiments, periosteum tissue is utilized as a source of mesenchymal stem cells and/or growth factors in a demineralized bone composition.

In some embodiments, an implant comprising biologically active material may be implanted or injected directly to a surgical site on a patient. In some embodiments, the implantable composite is configured to release biologically active material in the form of a depot. In various embodiments, a plurality of depots (e.g., pellets) can be administered to a surgical site. In some embodiments, a plurality of matrices are provided (e.g., in a kit) and administered to a surgical site and triangulate and/or surround the site needed for bone growth. In various embodiments, a plurality of matrices comprise about 1, 2, 3, 4, 5, 6, 7, 8, 9 or 10 depots. In some embodiments, a plasticizer is used to lower glass transition temperature in order to affect stability of the implant.

Radiographic markers can be included on the implantable composite to permit the user to position it accurately into the target site of the patient. These radiographic markers will also permit the user to track movement and degradation of the implantable composite at the site over time. In this embodiment, the user may accurately position the implantable composite in the site using any of the numerous diagnostic imaging procedures. Such diagnostic imaging procedures include, for example, X-ray imaging or fluoroscopy. Examples of such radiographic markers include, but are not limited to, ceramics, barium, phosphate, bismuth, iodine, tantalum, tungsten, and/or metal beads or particles. In various embodiments, the radiographic marker could be a spherical shape or a ring around the implant. The ceramic in the composition can also be used as a radiographic marker.

In some embodiments, the implantable composite comprising the biologically active material can be administered to the target site by being shaped according to the needs of a medical procedure and passed through a "cannula" or "needle" that can be a part of a delivery device e.g., a syringe, a gun delivery device, or any medical device suitable for the delivery of the implantable composite to a targeted organ or anatomic region. The cannula or needle of the device is designed to cause minimal physical and psychological trauma to the patient.

Method of Making Matrix

In some embodiments, the matrix is made by adding a biologically active material in an amount of about 20 wt % to about 90 wt % to a biodegradable polymer, the biodegradable polymer being in an amount of about 0.1 wt % to about 20 wt % based on the total weight of the implantable composite to form a mixture. In some embodiments, the mixture forms a slurry. The porous ceramic particles are added to the mixture to form the implant, the porous ceramic particles being in an amount of about 30 wt % to about 99.5 wt % based on a total weight of the implant. In some embodiments, the matrix is dried, hardened or cured to form the implant.

In some embodiments, in manufacturing the implant, a mixture of the matrix material (e.g., collagen and biologically active material) is combined with the mineral particles and a liquid to wet the material and form a putty or paste. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to the molding operation. Once wetted, the implantable composite becomes moldable and may be shaped by a medical practitioner by hand.

In one embodiment of manufacture, a collagen mixture can be combined with mineral particles, a biologically active material and a liquid, desirably with an aqueous preparation, to form a moldable cohesive mass. Excess liquid can be removed by any suitable means, including for example by applying the cohesive mass to a liquid-permeable mold or form and draining away excess liquid.

In some embodiments, the implantable composite is formed by mixing the mineral particles, polymer and the biologically active material until a coherent mass is formed. In some embodiments, the mineral particles, polymer and the biologically active material are wetted and mixed in a mixing syringe or device.

In some embodiments, the mixture of the polymer, mineral particles and/or biologically, active material are molded to take the form of the implant. Before, during or after molding, including in some instances the application of compressive force to the matrix, the biodegradable polymer can be subjected to one or more additional operations such as heating, lyophilizing and/or crosslinking. In this regard, crosslinking can be used to improve the strength of the formed matrix. Alternatively, the surface of the matrix can be crosslinked to reduce the size of the pores of the porous interior and thereby form the exterior of the matrix that is less permeable and/or less porous than a porous interior. Crosslinking can be achieved, for example, by chemical reaction, the application of energy such as radiant energy (e.g., UV light or microwave energy), drying and/or heating and dye-mediated photo-oxidation; dehydrothermal treatment; enzymatic treatment or others.

In some embodiments, the matrices are formed by mixing the biologically active material with a polymer slurry such as collagen and pouring into a shaped mold. The implantable composite mixture is freeze-dried and possibly chemically crosslinked and cut to the final desired shape.

The implantable composite may be used to repair bone and/or cartilage at a target tissue site, e.g., one resulting from injury, defect brought about during the course of surgery, infection, malignancy or developmental malformation. The implantable composite can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; or cosmetic procedures. Specific bones which can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Additional Therapeutic Agents

In some embodiments, The implantable composite further comprises biologically active material and one or more additional therapeutic agents including one or more growth factors, statins, etc. Isolated osteoinductive agents that are included within a matrix are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated. BMP osteoinductive agents may be administered as polynucleotides, polypeptides, full length protein or combinations thereof.

Indeed, the preferred osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, preferably near 1.5 mg/ml. However, any bone morphogenetic protein is contemplated including bone morphogenetic proteins designated as BMP-1 through BMP-18. BMPs are available from several sources, including Pfizer (Cambridge, Mass.), and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In addition to the above, the matrix may include one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The growth factors and the biologically active material of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such as Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11. (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NT kappa B inhibitors such as antioxidants, such as dithiocarbamate, and other compounds, such as, for example, sulfasalazine, statins or the like.

Examples of therapeutic agents suitable for use also include, but are not limited to, an anti-inflammatory agent, analgesic agent, or osteoinductive growth factor or a combination thereof.

Sterilization

The biodegradable polymer, mineral particles, biologically active material and devices to administer the implantable composite can be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device.

Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

All patent and non-patent publications cited in this disclosure are incorporated herein in to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable composite comprising a plurality of resorbable ceramic particles, the resorbable ceramic particles comprising carbonated hydroxyapatite and tricalcium phosphate in a ratio from about 5:95 to about 70:30, wherein the resorbable ceramic particles are granules having an average diameter in the range from about 1.5 to about 3.5 mm.

2. An implantable composite of claim 1, wherein the implantable composite comprises a biodegradable polymer and the tricalcium phosphate is β tricalcium phosphate.

3. An implantable composite of claim 1, wherein a resorption rate of the implantable composite containing the carbonated hydroxyapatite increases from about 10% to about 40% when compared to a resorption rate of an implantable composite having resorbable ceramic particles comprising hydroxyapatite and .beta. tricalcium phosphate in a ratio from about 5:95 to about 70:30 but no carbonated hydroxyapatite.

4. An implantable composite of claim 2, wherein the biodegradable polymer comprises one or more poly(L-lactide-co-D,L-lactide), polyglyconate, poly(acrylates), poly (anhydrides), poly(hydroxy acids), polyesters, poly(orthoesters), poly(alkylene oxides), polycarbonates, poly (propylene fumarates), poly(propylene glycol-co fumnaric acid), poly(caprolactones), polyamides, polyesters, polyethers, polyureas, polyamines, polyamine acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxy-butyrate/valerate copolymers, poly(vinyl pyrrolidone), polcyanoacrylates, polyurethanes, and polysaccharides, or combinations thereof.

5. An implantable composite of claim 2, wherein (i) the biodegradable polymer comprises soluble collagen and insoluble collagen in a ratio of about 30:70; or (ii) the biodegradable polymer comprises only insoluble collagen.

6. An implantable composite of claim 1, wherein the plurality of resorbable ceramic particles comprise carbonated hydroxyapatite and tricalcium phosphate in a ratio of from about 99:1 to about 1:99 by weight of the implantable composite.

7. An implantable composite of claim 1, further comprising bone-derived material, the bone-derived material comprising non-demineralized bone particles, demineralized bone particles, deorganified bone particles, partially demineralized bone particles, superficially demineralized bone particles, an organic bone particles, or combinations thereof.

8. An implantable composite of claim 1, which further comprises one or more of an initiator, accelerator, catalyst, solvent, wetting agent, lubricating agent, labeling agent, plasticizer, radiopacifier, porogen, bioactive agent, biostatic agent, cell, polynucleotide, protein, pharmaceutical agent or pharmaceutically acceptable excipient.

9. An implantable composite of claim 1, wherein the implantable composite is configured to be moldable after being wetted with a fluid, the fluid comprising water, sodium chloride, Lactated Ringer's solution, blood, marrow, bone marrow aspirate, bone marrow concentrate, autograft bone, or a combination thereof.

10. An implantable composite configured to fit at or near a bone defect site to promote bone growth, the implantable composite comprising: a biodegradable polymer and a plurality of resorbable ceramic particles, the resorbable ceramic particles comprising mixed AB type carbonated hydroxyapatite and tricalcium phosphate in a ratio from about 5:95 to about 70:30, wherein the resorbable ceramic particles are granules having a particle size from about 1.5 to about 1.6 mm.

11. An implantable composite of claim 10, wherein the tricalcium phosphate is β tricalcium phosphate.

12. An implantable composite of claim 1 wherein (i) the implantable composite is configured to be moldable after being wetted with a fluid or (ii) the implantable composite further comprises autograft bone or autologous bone.

13. An implantable composite of claim 12, wherein the fluid comprises water, sodium chloride, Lactated Ringer's solution, blood, marrow, bone marrow aspirate or a combination thereof.

14. An implantable composite of claim 10, wherein the biodegradable polymer comprises soluble collagen and insoluble collagen, the soluble collagen and insoluble collage being in a ratio of about 30:70.

15. A method of treating a bone cavity in a subject in need thereof, the method comprising implanting into the bone cavity an implantable composite, the implantable composite comprising a plurality of resorbable ceramic particles and a biodegradable polymer, the resorbable ceramic particles comprising mixed AB type carbonated hydroxyapatite and β tricalcium phosphate in a ratio from about 5:95 to about 70:30, wherein the ceramic particles are granules having an average particle diameter in the range from about 1.5 to about 3.5 mm.

16. A method of treating according to claim 15, wherein the implanting comprises mixing the implantable composite with a fluid comprising water, sodium chloride, Lactated Ringer's solution, blood, marrow, bone marrow aspirate or a combination thereof.

17. A method of treating according to claim 15, wherein the biodegradable polymer comprises soluble collagen and insoluble collagen, the soluble collagen and insoluble collagen being in a ratio of about 30:70.

\* \* \* \* \*